(12) United States Patent
Ein-Gal

(10) Patent No.: US 8,368,042 B2
(45) Date of Patent: Feb. 5, 2013

(54) PHYSICAL WEDGE POSITIONING

(76) Inventor: Moshe Ein-Gal, Ramat Hasharon (IL)

( * ) Notice: Subject to any disclaimer, the term of this patent is extended or adjusted under 35 U.S.C. 154(b) by 94 days.

(21) Appl. No.: 12/945,899

(22) Filed: Nov. 15, 2010

(65) Prior Publication Data
US 2012/0119120 A1 May 17, 2012

(51) Int. Cl.
*G02B 5/00* (2006.01)
(52) U.S. Cl. .................................. 250/505.1
(58) Field of Classification Search .............. 250/505.1, 250/515.1, 492.3, 492.1, 396 R; 378/159, 378/64, 65
See application file for complete search history.

(56) References Cited

U.S. PATENT DOCUMENTS

| | | | | |
|---|---|---|---|---|
| 4,400,827 A | * | 8/1983 | Spears | 378/207 |
| 4,868,843 A | * | 9/1989 | Nunan | 378/152 |
| 4,983,849 A | * | 1/1991 | Thompson et al. | 250/492.3 |
| 6,304,628 B1 | * | 10/2001 | Steinberg | 378/65 |
| 6,891,178 B2 | * | 5/2005 | Xing | 250/505.1 |
| 7,834,336 B2 | * | 11/2010 | Boeh et al. | 250/505.1 |
| 7,977,656 B2 | * | 7/2011 | Fujimaki et al. | 250/492.3 |
| 2003/0099454 A1 | * | 5/2003 | Chang | 385/140 |
| 2006/0033042 A1 | * | 2/2006 | Groezinger et al. | 250/492.1 |
| 2008/0067385 A1 | * | 3/2008 | Tokuda et al. | 250/310 |
| 2009/0189095 A1 | * | 7/2009 | Flynn et al. | 250/492.3 |
| 2010/0019167 A1 | * | 1/2010 | Al-Sadah et al. | 250/396 R |
| 2010/0127192 A1 | * | 5/2010 | Ein-Gal | 250/505.1 |
| 2010/0260319 A1 | * | 10/2010 | Ein-Gal | 378/65 |
| 2011/0204260 A1 | * | 8/2011 | Ein-Gal | 250/492.1 |

OTHER PUBLICATIONS

Instruction Manual and Experiment Guide for the PASCO scientific Model WA-9314B, PASCO Scientific, Copywrite 1991.*

* cited by examiner

*Primary Examiner* — Robert Kim
*Assistant Examiner* — Jason McCormack
(74) *Attorney, Agent, or Firm* — Dekel Patent Ltd.; David Klein

(57) ABSTRACT

A method for modulating a radiation beam toward a target, including rotating a radiation beam gantry through an arc segment while irradiating a target with a radiation beam, placing a physical wedge in a beam path of the radiation beam to modify at least one of a beam aperture and a beam intensity of the radiation beam while rotating through the arc segment, and modifying at least one of a wedge angle and a wedge orientation of the physical wedge during a temporal increment associated with the arc segment.

7 Claims, 3 Drawing Sheets

PHYSICAL WEDGE POSITIONING

FIELD OF THE INVENTION

The present invention generally relates to a system and method for radiation therapy or diagnostics with beam modulation, such as but not limited to, intensity modulated radiation therapy (IMRT) or diagnostics, and particularly to positioning a physical wedge to modulate the radiation beam.

BACKGROUND OF THE INVENTION

Radiation-emitting devices are well known and used for radiation therapy or diagnostics. Typically, a radiation therapy device includes a gantry which can be swiveled around a horizontal axis of rotation in the course of a therapeutic treatment. A linear accelerator is located in the gantry for generating a high-energy radiation beam for therapy. This high radiation beam can be an electron radiation or photon (X-ray) beam. Other radiation beam sources can be used as well. During treatment, the radiation beam is typically directed at the isocenter of gantry rotation.

The goal of radiation treatment planning is to maximize the dose to the target volume while protecting radiation sensitive healthy tissue. The X-ray bean intensity often varies over the treatment field by placing an X-ray absorber in the beam path. This allows the target volume to be placed in regions of high beam intensity, while the surrounding radiation sensitive tissue is protected by placement in low intensity regions.

One known device for beam modulation is a wedge (wedge-shaped absorber), used to shape the dose distribution from external photon beams, for example. It is available on the radiation therapy machines of all major manufacturers. The most basic form of wedge is the physical wedge, made of metals such as lead or stainless steel. The physical wedge is placed in the beam path and exponentially decreases the beam intensity laterally across the treatment field. The "toe" of the wedge (i.e., where the thickness of the wedge is the smallest) produces a high beam intensity region, since this portion of the beam has the least attenuation.

An external physical wedge is mounted outside the machine head. A set of standard wedge angles, typically 15°, 30°, 45°, and 60° are exchangeable. A single internal wedge of 60°, called the 'universal' wedge, is also used: the wedge is mounted inside the machine head and wedge angles less than 60° are obtained by combining a 60° wedge field and an open field with weights determined by the desired wedge angle. For example, a 30° equivalent wedge is obtained by irradiating half the time with the 60° wedge and half the time with an open field. Since positioning the wedge in place is slow, the beam is turned off during the wedge motion. The movements of a wedge into in-beam position and subsequently into out-of-beam position are in opposite directions. While the wedge functions properly when stationary, un-compensated radiation would be delivered if radiation is applied during wedge motion.

An 'Omni' wedge implements wedge orientation by combining weighted orthogonal wedged fields. A 'Super-Omni' wedge implements wedging of desired angle and orientation by combining weighted 'Omni' wedge and an open field.

The physical wedge has some disadvantages, however. The primary beam intensity is reduced at the target volume; thus, treatment times are increased. Further, scattering of the beam outside the treatment field causes an additional dose to be delivered outside the target volume. It also introduces a spatial energy dependence (i.e., hardness) to the beam, affecting the depth at which the radiation is absorbed across the treatment field. Additional time and effort are required to design, validate, manufacture, install/remove, and store the accessories. In addition, only a limited number of wedge angles are available.

Non-physical wedging is implemented by moving a uniformly attenuating object, e.g., a collimator jaw, across the field in controlled speed and dose rate determining the wedge angle. Non-physical 'Super Omni' wedge may produce wedging of desired angle and orientation by using an arrangement of four movable jaws and an open field, whereas the respective fields are properly weighted.

Implementing combinations of sequentially-irradiated fields may be slow and cumbersome. For example, typical jaws speed is in the range of several cm/sec. The time required for a jaw to cover a field-width may be on the order of several seconds.

Arc treatment is an irradiation method where the orientation of the target to the radiation source varies continuously during irradiation. An arc treatment field involves, inter alia, a treatment delivered by continuous rotation of a radiation beam gantry through an angular arc segment while radiation is being applied. Beam aperture and intensity level may be modified for each arc segment. A typical arc segment is on the order of several degrees and the associated time increment is on the order of a second.

SUMMARY OF THE INVENTION

The present invention seeks to provide improved wedging method and apparatus, as is described more in detail hereinbelow.

There is thus provided in accordance with an embodiment of the present invention a method for modulating a radiation beam toward a target, including rotating a radiation beam gantry through an arc segment while irradiating a target with a radiation beam, placing a physical wedge in a beam path of the radiation beam to modify at least one of a beam aperture and a beam intensity of the radiation beam while rotating through the arc segment, and modifying at least one of a wedge angle and a wedge orientation of the physical wedge during a temporal increment associated with the arc segment, wherein the temporal increment includes five sequential sub-increments defined as:

1) Pre-position—wherein the wedge is at rest outside a treatment field,
2) Approaching—wherein the wedge moves toward a desired wedging position,
3) Wedging—wherein the wedge is in the desired position,
4) Clearing—wherein the wedge moves away from the desired wedging position, and
5) Post-position—wherein the wedge is at rest outside the field.

In accordance with an embodiment of the present invention the wedge orientation is modified by rotating the wedge about a rotational axis intersecting the wedge, such as when the wedge is not in the beam path. After rotating the wedge, the wedge can be moved through the Approaching, Wedging and Clearing sub-increments.

In accordance with an embodiment of the present invention a constant beam intensity and a constant Moving velocity are maintained (Moving being a combination of the Approaching and Clearing sub-increments).

In accordance with an embodiment of the present invention the method includes representing the wedge by two virtual orthogonal wedges and combining deviations respectively associated with the orthogonal wedges to obtain a wedge deviation due to motion.

There is also provided in accordance with an embodiment of the present invention a modulation system for modulating a radiation beam toward a target, including a rotational stage for supporting and orienting a physical wedge, the rotational stage having a rotational axis that intersects the physical wedge, a mover operable to move the rotational stage into and out of a beam path of a radiation beam, and a controller in communication with the rotational stage and the mover.

In accordance with an embodiment of the present invention the mover is operable to move the rotational stage into and out of the beam path in generally the same direction.

In accordance with an embodiment of the present invention a radiation source operable to emit a radiation beam towards a target.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
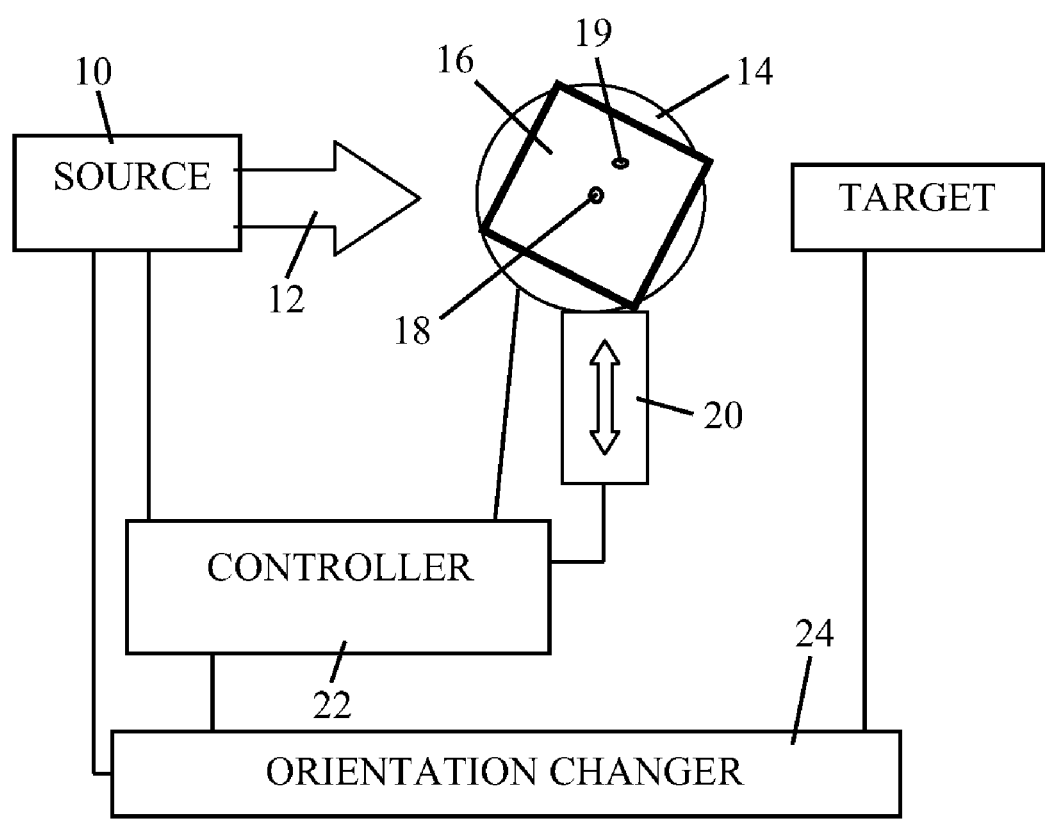
FIG. 1 is a simplified illustration of a system for modulating a radiation beam toward a target, in accordance with an embodiment of the present invention.

Reference is now made to FIG. 1, which illustrates a system for modulating a radiation beam toward a target, in accordance with an embodiment of the present invention. The system may include only the elements for modulating or it may also include a radiation source 10 operable to emit a radiation beam 12 towards a target.

In accordance with an embodiment of the present invention, the modulation system includes a rotational stage 14 for supporting and orienting a physical wedge 16. The rotational stage 14, which may be a turntable, for example, has a rotational axis 18 that intersects the physical wedge 16 (such as being perpendicular to the plane of the drawing sheet and in the center of wedge 16; the rotational axis 18 may be optionally off-center in another embodiment, as indicated at 19). A mover 20, such as but not limited to, a linear actuator, is operable to move rotational stage 14 into and out of a beam path of radiation beam 12. A controller 22 is in communication with rotational stage 14, mover 20 and radiation source 10.

In accordance with an embodiment of the present invention, mover 20 is operable to move rotational stage 14 into and out of the beam path in generally the same direction.

An orientation changer 24, such as but not limited to, a gantry and/or turntable, is operable to change the relative orientation of the beam and the target.

Figure 2:
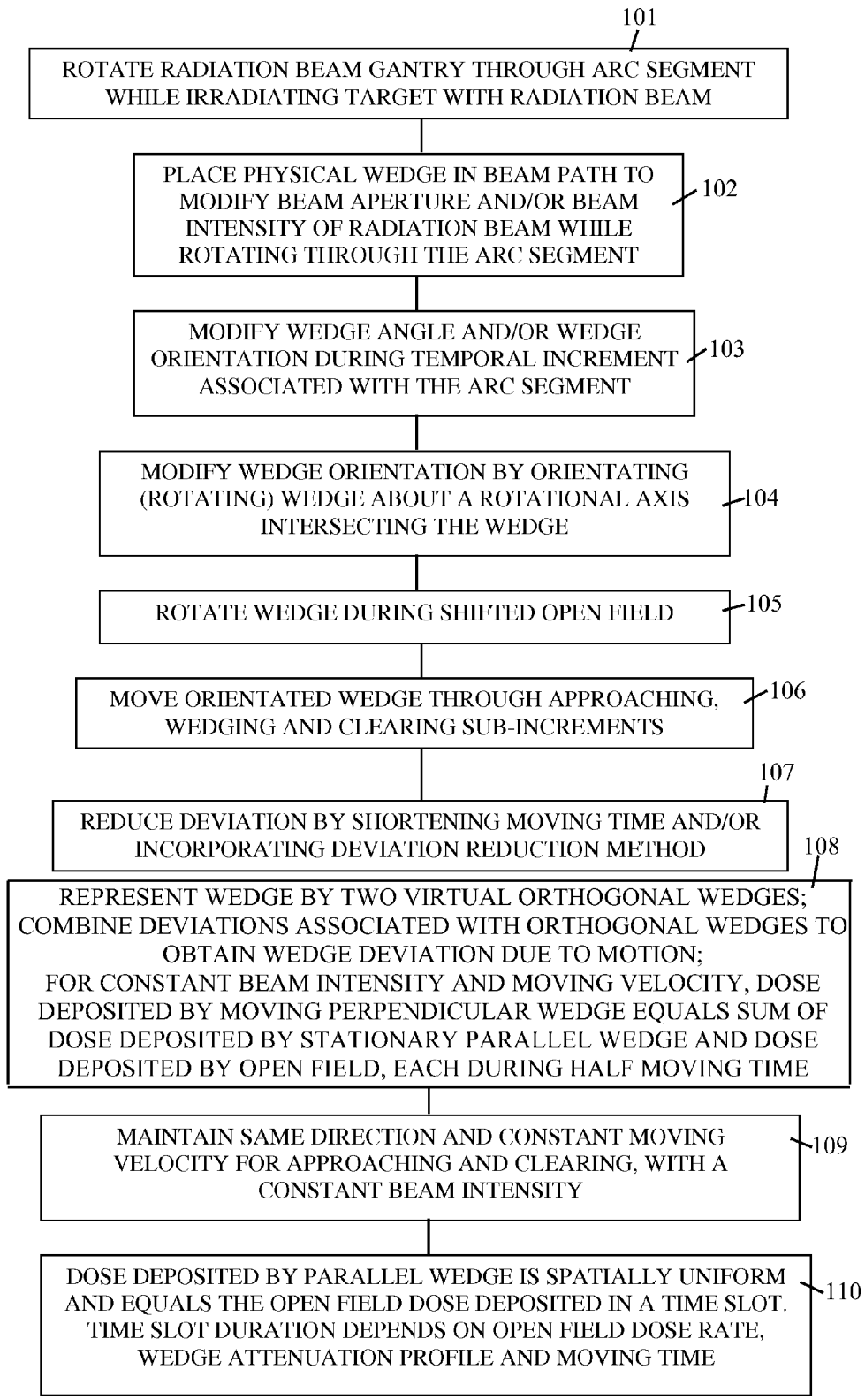
FIG. 2 is a simplified flow chart of a method for modulating a radiation beam toward a target, in accordance with an embodiment of the present invention.

Reference is now made to FIG. 2, which illustrates a flow chart of a method for modulating a radiation beam toward a target, in accordance with an embodiment of the present invention.

A radiation beam gantry is rotated through an arc segment while irradiating a target with the radiation beam (101).

The physical wedge is placed in a beam path of the radiation beam to modify a beam aperture and/or a beam intensity of the radiation beam while rotating through the arc segment (102).

Figure 3:
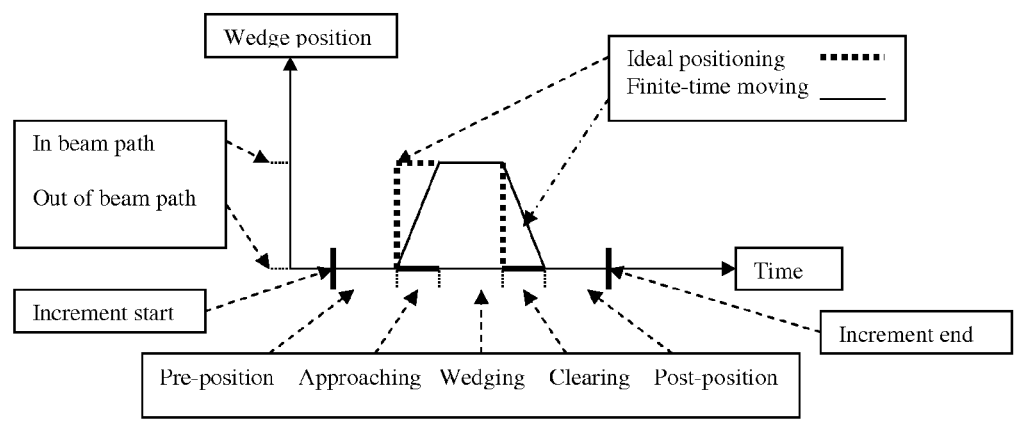
FIG. 3 is a simplified graphical illustration of a temporal increment, which includes five sequential sub-increments, in accordance with an embodiment of the present invention.

A wedge angle and/or a wedge orientation of the physical wedge are modified during a temporal increment associated with the arc segment (103). The temporal increment includes five sequential sub-increments defined as (see FIG. 3):

1) Pre-position—wherein said wedge is at rest outside a treatment field;

2) Approaching—wherein said wedge moves toward a desired wedging position;

3) Wedging—wherein said wedge is in the desired position;

4) Clearing—wherein said wedge moves away from the desired wedging position; and 5) Post-position—wherein said wedge is at rest outside the field.

Definitions:

Moving—concatenated (combination of) Approaching and Clearing.

Moving time—the total time for Moving

Ideal positioning—positioning with zero Moving time.

Wedge motion coordinate system—the beam coordinate system.

Open field—pre-position and post-position of same temporal increment.

Shifted open field—post-position of a temporal increment and pre-position of the subsequent one.

In accordance with an embodiment of the present invention, the wedge orientation is modified by orientating (rotating) the wedge about a rotational axis intersecting the wedge (104). Rotating the wedge takes place during the shifted open field, that is, when the wedge is not in the beam path (105). The orientated wedge then moves through Approaching, Wedging and Clearing sub-increments (106).

Since wedge Moving takes place during irradiation, dose deposited during the finite Moving time may introduce deviation from ideal positioning dose. Deviation may be reduced by shortening the Moving time and/or incorporating a deviation reduction method (107).

An example of such a method is based on the 'Omni' wedge principle, which states the equivalence, relative to accumulated fluence, of a wedge in a given orientation and a weighted combination of orthogonal wedges. Accordingly, a wedge can be represented by two virtual orthogonal wedges and the respective deviations associated with the orthogonal wedges can be combined to obtain the wedge deviation due to motion. For a moving wedge, the orthogonal virtual wedges are respectively selected to be perpendicular and parallel to the wedge motion. Evaluation of deviations associated with the perpendicular and the parallel wedges follows for a wedge moving in a constant velocity during Moving while being irradiated by a spatially uniform and temporally constant beam intensity:

The accumulated fluence produced by the perpendicular wedge during Moving equals that produced by an open field combined with that produced by a stationary perpendicular wedge, each during half the Moving time (108).

Since Moving time amounts to reducing Wedging time and Open field time respectively by half a Moving time each, it follows that the perpendicular wedge introduces no dose deviation regardless of Moving time. The total deviation is then reduced to the one produced by the parallel virtual wedge.

In accordance with another embodiment of the present invention, a constant Moving velocity (including direction) and a spatially uniform and temporally constant beam intensity are maintained for Approaching and Clearing (109).

The accumulated fluence produced by the parallel wedge during Moving is spatially uniform and, therefore, equals the Open field fluence accumulated in a time slot, where the time slot duration depends on the open field dose rate, the wedge attenuation profile and the Moving time (110). The deviation related to the parallel wedge can then be calculated and corrected by modifying the open field time and the Wedging time relative to the respective ones selected for ideal positioning.

The following parameters are defined:
R=ratio of the time slot duration to the temporal increment
A=ratio of Wedging time to open field time for ideal positioning, and
A'=corresponding ratio for finite Moving time, i.e., finite R.

A' is derived from the following conditions related to the ideal positioning:

$$\text{Temporal increment} = \text{wedging time} + \text{open field time} \quad (a)$$

$$\text{(b)} \quad \frac{\text{wedging time} + \text{time slot}}{\text{open field time} - \text{time slot}} = A$$

The solution for A' is:

$$A' = \frac{A(1-R)+R}{1-R+AR}$$

from which formulas for the modified Wedging and Open field times associated with finite R are derived:

(Modified open field time)=(Ideal positioning open field time)(1+A)/(1+A')·(Modified wedging time) =(The temporal increment)−(Modified open field time).

In accordance with another embodiment of the present invention, the formulas are applied for determining Wedging and Open field times for a desired wedge angle, taking into account the finite wedge Moving time.

The requirement for constant wedge velocity during Approaching and Clearing can be relaxed. For example, for identical velocity profiles for Approaching and Clearing, the perpendicular wedge introduces a weighted combination of uniform field and stationary wedging, thus the associated ideal positioning timing can be modified for finite Moving time as described. In general, a deviation produced by variable velocity profiles and/or variable beam intensity includes components of uniform dose distribution and desired wedged fluence. Knowing the system parameters, these components can be eliminated by modifying the ideal open field and wedging times as described above, thus reducing the deviation.

In accordance with yet another embodiment of the present invention, the requirements for constant velocity or constant beam intensity are eliminated.

The scope of the present invention includes both combinations and subcombinations of the features described hereinabove as well as modifications and variations thereof which would occur to a person of skill in the art upon reading the foregoing description and which are not in the prior art.

What is claimed is:

1. A method for modulating a radiation beam toward a target, comprising;
    rotating a radiation beam gantry and/or a target through an arc segment while irradiating the target with the radiation beam;
    placing a physical wedge in a beam path of said radiation beam to modify at least one of a beam aperture and a beam intensity of said radiation beam while rotating through said arc segment; and
    modifying at least one of a wedge angle and a wedge orientation of said physical wedge during a temporal increment associated with said arc segment, wherein said temporal increment comprises five sequential sub-increments defined as:
    1) Pre-position—wherein said wedge is at rest outside a treatment field;
    2) Approaching—wherein said wedge moves toward a desired position;
    3) Wedging—wherein said wedge is in the desired position;
    4) Clearing—wherein said wedge moves away from the desired position; and
    5) Post-position—wherein said wedge is at rest outside the field, wherein wedge angle is determined by times of the sub-increments;
    And comprising modifying said wedge orientation by rotating said wedge about a rotational axis intersecting said wedge, and wherein Moving is a combination of the Approaching and Clearing sub-increments, and a ratio for finite Moving time (A') is calculated from;
    R=ratio of a duration of a time slot to the temporal increment, wherein said time slot duration depends on an open field dose rate, a wedge attenuation profile and the Moving time
    A=ratio of Wedging time to open field time for ideal positioning, and
    (a) Temporal increment =wedging time +open field time $$\frac{\text{wedging time} + \text{time slot}}{\text{open field time} - \text{time slot}} = A \quad (b)$$

and A' is calculated as:

$$A' = \frac{A(1-R)+R}{1-R+AR}.$$

2. The method according to claim 1, comprising rotating said wedge when said wedge is not in the beam path.

3. The method according to claim 2, wherein after rotating said wedge, moving said wedge through said Approaching, Wedging and Clearing sub-increments.

4. The method according to claim 1, comprising maintaining substantially spatially uniform and temporally constant beam intensity and a constant Moving velocity.

5. The method according to claim 1, comprising representing the wedge by two virtual orthogonal wedges and combining deviations respectively associated with the orthogonal wedges to obtain a wedge deviation due to motion.

6. The method according to claim 1, wherein an accumulated fluence produced by the wedge during Moving is spatially uniform.

7. The method according to claim 1, wherein modified Wedging and Open field times associated with finite R are derived as:
    (Modified open field time) =(Ideal positioning open field time)(1+A)/(1+A'). (Modified wedging time) =(The temporal increment) −(Modified open field time).

* * * * *